United States Patent [19]

Baldwin

[11] 4,263,307

[45] Apr. 21, 1981

[54] N-ARALKYL CONTAINING CYANOPYRIDINES

[75] Inventor: John J. Baldwin, Lansdale, Pa.

[73] Assignee: Merck & Co., Inc., Rahway, N.J.

[21] Appl. No.: 63,019

[22] Filed: Aug. 2, 1979

Related U.S. Application Data

[62] Division of Ser. No. 919,646, Jun. 27, 1978.

[51] Int. Cl.$^3$ .................... A61K 31/44; C07D 213/85
[52] U.S. Cl. .................................... 424/263; 546/288; 546/269
[58] Field of Search .................... 546/288; 424/263

[56] References Cited

U.S. PATENT DOCUMENTS 4,151,284   4/1979   Baldwin ............................. 546/288

Primary Examiner—Henry R. Jiles
Assistant Examiner—Robert C. Whittenbaugh
Attorney, Agent, or Firm—Daniel T. Szura; Harry E. Westlake, Jr.

[57] ABSTRACT

N-Aralkylamino-OR-propoxycyanopyridines having pharmacological activity are disclosed.

9 Claims, No Drawings

N-ARALKYL CONTAINING CYANOPYRIDINES

This is a division of application Ser. No. 919,646, filed June 27, 1978.

BACKGROUND OF THE INVENTION

The present invention is concerned with N-aralkylamino-OR-propoxycyanopyridines. These pyridines have useful pharmaceutical activity, e.g., as antihypertensive agents.

N-Aklyl-OR-propoxycyanopyridines are taught in U.S. Pat. No. 4,000,282 and U.S. Pat. No. 4,053,605 to be useful antihypertensive agents. These compounds also have β-adrenergic blocking activity. Certain N-aralkylhydroxypropoxy-substituted heterocyclics are also disclosed in South African Pat. No. 741070 and are taught, among other things, to have β-adrenergic blocking activity.

N-Aralkylamino-OR-propoxycyanopyridines have been discovered which are useful as antihypertensive agents.

SUMMARY OF THE INVENTION

N-Aralkylamino-OR-propoxycyanopyridines wherein said alkyl group is linear and their use as pharmaceutical agents.

DESCRIPTION OF THE PREFERRED EMBODIMENTS

An embodiment of the present invention is compounds having the formula

$$R_a\text{—O—CH}_2\text{—CHOR—CH}_2\text{—NHR}^1 \quad (I)$$

and pharmaceutically acceptable salts thereof wherein $R_a$ is

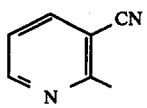

R is H or

wherein L is $C_1$-$C_{10}$ alkyl, phenyl or substituted phenyl having one or two substituents which are independently selected from $C_1$-$C_4$ alkyl, $C_1$-$C_4$ alkoxy or halo
and
$R^1$ is a phenyllinearalkyl group having the formula

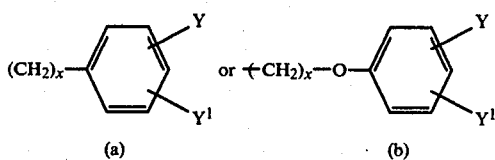

wherein x is 1 to 4 and
Y and $Y^1$, when separate, are H, —OCH$_3$, OH or halo and when joined, form

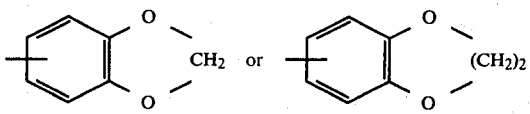

with the phenyl group.
R is h or the

group, with H being preferred. The L group includes $C_1$-$C_{10}$, linear and branched hydrocarbon alkyl such as methyl, n-decyl, tert butyl, isoamyl, n-heptyl and the like with $C_1$-$C_4$ alkyl being preferred, and phenyl or mono and disubstituted phenyl such as tert butylphenyl, 2,6-dibromophenyl, 3-methylphenyl, 4-n-propylphenyl, 3,5-dimethoxyphenyl, 4-iodophenyl, 2-methyl-4-chlorophenyl, 4-fluorophenyl and the like, with monosubstituted phenyl preferred.

Y and $Y^1$ may also be joined to form the dioxy alkylene moiety -O-(CH$_2$)$_{1 \text{ or } 2}$-O- which is attached to the phenyl ring to form a bicyclic group of the formula

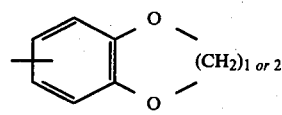

Preferred positioning of the dioxyalkylene moiety is

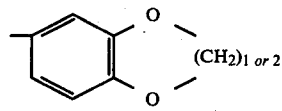

The alkylene group, —(CH$_2$)$_x$— may have from 1 to 4 units, with 1-2 being preferred.

One class of preferred compounds are those of formula I where
$R^1$ is

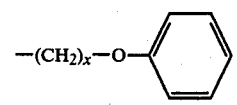

In more preferred compounds of this class, x is 1-2.
Another class of preferred compounds are those of formula I where
$R^1$ is

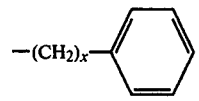

In more preferred compounds, x is 2 and Y and $Y^1$ are selected from H and —OCH$_3$, and especially where Y is H and $Y^1$ is OCH$_3$, Y and $Y^1$ are both OCH$_3$, or Y and $Y^1$ are both H.

The pyridines of formula I have a chiral center at the 2-position in the propoxysubstituent, which confers optical activity. All the optical isomer forms, that is mixtures of enantiomers, e.g., racemates as well as the individual enantiomers of Formula are included. These individual enantiomers of Formula I are commonly designated according to the optical rotation they effect by (+) and (−), (L) and (D), (l) and (d) or combinations of these symbols. These isomers may also be designated according to their absolute spatial configuration by (S) and (R) which stand for sinister and rectus, respectively. Where no symbol is used in naming a compound, the compound is a racemate. The (S) isomer is a preferred isomer configuration.

The pyridines of the present invention can be prepared by any convenient process.

One such process involves the coupling of a halopyridine with a suitable substituted oxazolidine and hydrolyzing the reaction product obtained. This process is illustrated by the following set of reaction equations:

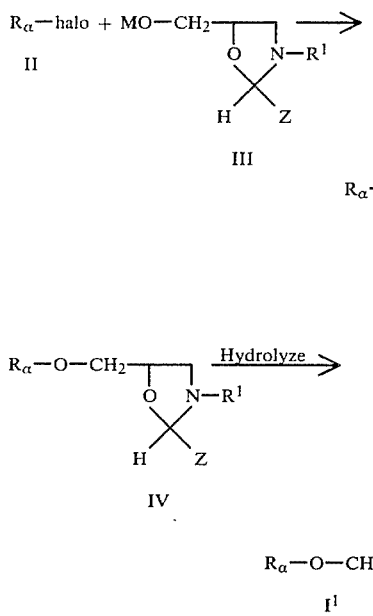

Halo may be Cl, Br, F and I, with Cl being preferred. M is an alkali metal, with potassium or sodium. Z can be hydrogen or the residue of any suitable aldehyde

e.g., an arylaldehyde, such as benzaldehyde, napthaldehyde and the like, or an alkanal such as acetaldehyde, butyraldehyde and the like. The process for preparing oxazolidines where M is hydrogen is disclosed in U.S. Pat. No. 3,718,647 and U.S. Pat. No. 3,657,237 and to the extent necessary the pertinent disclosure is incorporated herein by reference. The alkali metal salt of the oxazolidine is prepared in a conventional manner by reaction of the corresponding hydroxymethyloxazolidine with an appropriate amount of an alkali base reactant. However, this Reaction A may also be carried out with in-situ formation of the alkali metal oxazolidine salt (Formula III) by reacting the oxazolidine

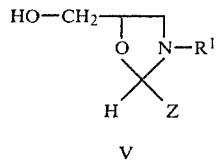

with the Formula II pyridine in the presence of a strong base such as an alkali metal alkoxide (e.g., K—O—C—(CH$_3$)$_3$) or sodium hydride.

The coupling reaction can be carried out at temperatures ranging from about 0° C. to the reflux temperature of the solvent. A temperature range of about 10° C. to about 75° C. is preferred. The reaction is generally carried out in a solvent. Any suitable solvent may be used. Examples of useful solvents are dimethylformamide, dimethylsulfoxide, hexamethylphosphoramide, tert butanol, alkanols and the like. The hydrolysis is carried out using conventional acid hydrolysis reagent and techniques, e.g., treatment with a solution of an acid such as acetic acid or any strong mineral acid such as HCl or H$_2$SO$_4$. The hydrolysis product can be directly obtained as the salt of the acid used for the hydrolysis. Ordinarily, the product I is recovered as the free base after conventional neutralization of the salt.

The coupling reaction is ordinarily carried out at atmospheric pressure. Higher pressures may be used if desired.

When a racemic oxazolidine (Formula III or V) is used as a reactant, the product is obtained as a racemate. The racemate may be separated into its individual enantiomers by conventional resolution techniques, e.g., using an enantiomer of a suitable optically active organic acid such as tartaric acid.

When Z in the oxazolidine, i.e., Formula III, IV or V, is other than hydrogen, in addition to the chiral center at oxazolidine position 5 there is a second chiral center at position 2. However, whenever the oxazolidine is designated, e.g., as (S), (R) or (R,S), this designation refers only to the optical configuration around the carbon atom at the 5 position.

By using a single optical isomer of said oxazolidine in the above reactions, the product may be obtained directly as a single enantiomer. Thus, if the S-isomer of the oxazolidine is used, then the product obtained will be the S-isomer. This provides a convenient way for directly preparing individual isomers of the present pyridines.

Another convenient process for preparing the present pyridines is by treating an appropriate pyridine epoxide with a suitable amino as illustrated by the following reaction equation:

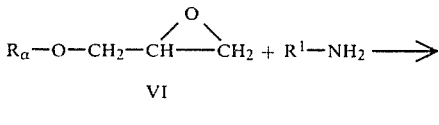

R$_a$—O—CH$_2$—CHOH—CH$_2$—NHR$^1$      (I$^1$)

This reaction is advantageously carried out in excess amine (R$^1$NH$_2$) reactant. Temperatures up to reflux can be used. An especially useful temperature range is room temperature to about 100° C. The reaction is conveniently carried out at room temperature.

The product from the eposide/$R^1NH_2$ reaction is ordinarily a racemate, and can be separated using conventional resolution procedures.

If a single optical isomer of the Formula VI epoxide is used, as the reactant, the product obtained is the corresponding single optical isomer, e.g.,

$$(S)-VI + R^1NH_2 \rightarrow (S)-I^1$$

The optically active epoxide intermediates of Formula VI can be prepared by the reaction illustrated below:

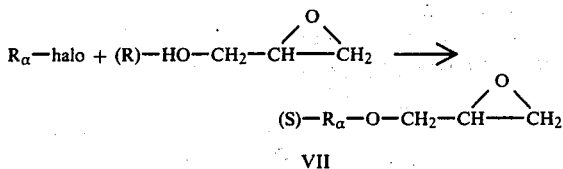

Pyridines of the present invention wherein R is other than hydrogen are conveniently prepared by treating the corresponding pyridine where R is hydrogen with an appropriate acylating agent such as an acyl halide, e.g., undecanoyl chloride, pivaloyl chloride, benzoyl-chloride, p-methoxybenzoyl chloride or an anhydride, e.g., acetic anhydride, and the like. The reaction is illustrated by the following equations:

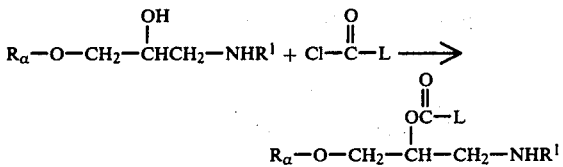

The compounds of the present invention also include the pharmaceutically acceptable salts of the present pyridines. These salts are generally salts of the Formula I pyridines and organic or inorganic acids. These salts are prepared by treating the pyridine with an appropriate amount of a useful acid, generally in a suitable solvent. Examples of useful organic acids are isethionic acid and carboxylic acids such as maleic acid, acetic acid, tartaric acid, propionic acid, fumaric acid, succinic acid, pamoic acid, oxalic acid, pivalic acid and the like; useful inorganic acids are hydrohalo acids such as HCl, HBr, HI; sulfuric acid, phosphoric acid and the like. The hydrochloride and hydrogen maleate salts are examples of preferred salts.

The compounds of the present invention have β-adrenergic blocking activity. This β-adrenergic blocking activity is determined by measuring the ability of representative pyridines to block the β-adrenergic stimulant effect of isoproterenol in a test animal.

In evaluating the β-blocking effectiveness of a representative compound, it was noted that the compound was more effective in blocking the heart rate increase caused by isoproterenol than it was in blocking the peripheral effects induced by isoproterenol.

The present pyridines also exhibit antihypertensive activity of immediate onset. This rapid onset anithypertensive activity is determined by administering a representative pyridine of the present invention to spontaneously hypertensive (SH) rats and measuring the effect on blood pressure.

The ability of the compounds of the present invention to reduce blood pressure in the SH rat indicates that the compounds and their salts may be useful to treat essential hypertension in humans.

The cardioselective, β-adrenergic blocking effectiveness of the present compounds indicates that they are useful in treating human cardiovascular conditions such as angina pectoris and arrhythmias, especially when effect on the pulmonary function must be minimized, e.g., in a patient who also has asthma.

For use as β-adrenergic blocking agents, and/or antihypertensive agents the compounds of the present invention can be administered orally, by inhalation, by suppository or parenterally, i.e., intravenously, intraperitoneally, etc., and in any suitable dosage form. The compounds may be offered in a form (1) for oral administration, e.g., as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material, or (2) for parenteral administration, dissolved, dispersed, or emulsified in a suitable liquid carrier or diluent or (3) as an aerosol or (4) as a suppository. The ratio of active ingredient (present pyridine) to compounding ingredients will vary as the dosage form requires. Conventional procedures are used to prepare the pharmaceutical formulations.

The effective daily dosage level for the present compounds may be varied from about 10 mg. to about 2000 mg. Daily doses ranging from about 50 to about 1000 mg. are preferred, with about 100 to about 500 mg. being a more preferred range. Oral administration is preferred. Either single or multiple daily doses may be administered depending on unit dosage.

Thus, another embodiment of this invention is a pharmaceutical composition containing β-adrenergic blocking or antihypertensive amount of a compound of the present invention.

The following examples illustrate the preparation of representative compounds of the present invention. Temperatures are in °Celsius.

EXAMPLE 1

(a) 3-(3,4-Dimethoxyphenethylamino)-1,2-propanediol

To a solution of 3,4-dimethoxypenethylamine (128.6 g, 0.71 m) in 150 ml of isopropanol was added dropwise and with stirring at 50° a solution of glycidol (15 g, 0.2 m) in 40 ml of isopropanol. After the addition was complete, the solution was heated 1 hr. at 50° and then allowed to stand 15 hr. at 25°. The solvent was removed under reduced pressure (24 mm); the excess 3,4-dimethoxyphenethylamine was then removed by distillation at 0.15 mm. The resulting residue was crystallized from toluene to yield 29 g of 3-(3,4-dimethoxyphenethylamino)-1,2-propanediol (m.p. 80°-82°).

(b) 2-Phenyl-3-(3,4-dimethylphenethyl)-5-hydroxymethyloxazolidine

A mixture of 3-(3,4-dimethoxyphenethylamino)1,2-propanediol (23 g, 0.09 m), benzaldehyde (21.3 g, 0.2 m), benzoic acid (500 mg) in benzene (75 ml) was heated at reflux with removal of water for 45 min. The mixture was washed with saturated aqueous solution of $Na_2CO_3$ then with a saturated aqueous solution of NaCl. The organic solution was dried over $Na_2SO_4$ and concentrated with removal of toluene and benzaldehyde yielding 31 g of 2-phenyl-3-(3,4-dimethylphenethyl)-5-hydroxymethyloxazolidine as residue.

(c) (R,S)-3-Cyano-2-[3-(3,4-dimethoxyphenethylamino)-2-hydroxypropoxy]-pyridine Hydrochloride To a solution of 2-phenyl-3-(3,4-dimethoxyphenethyl)-5-hydroxymethyloxazolidine (9 g, 0.026 m) in DMF (50 ml) at 80° was added 50% NaH in mineral oil (1.25 g). After 0.5 hr. at 80°, the solution was cooled to 25° and a solution of 2-chloro-3-cyanopyridine (7.28 g, 0.05 m) in DMF (50 ml) was added. The reaction mixture was heated at 80° for 2 hr. then at reflux for 22 hr. The solvent was removed under reduced pressure (25 mm) and the residue treated with 1 N HCl. After heating 0.5 hr. on a steam bath, the mixture was extracted with ether then made basic with a saturated aqueous solution of $Na_2CO_3$ and extracted with $CHCl_3$. The $CHCl_3$ solution was concentrated to yield an oil which was chromatographed on silica gel and eluted with chloroform saturated with ammonia to yield (R,S)-3-cyano-2-[3-(3,4-dimethoxyphenethylamino)-2-hydroxypropoxy] pyridine hydrochloride which was converted to the hydrochloride salt on treatment with methanolic HCl (290 mg; m.p. 132°–134°).

EXAMPLE 2

(S)-2-[3-(2-Methoxyphenethylamino)-2-hydroxy-1-propoxy]-3-cyanopyridine

A mixture of 2-methoxyphenethylamine (0.91 g, 6 mmole) and (S) -2-(2,3-epoxy-1-propoxy)-3-cyanopyridine (1.05 g, 6 mmole) was heated at 60° C. for 18 hr. Upon cooling, the material solidified. Recrystallization from toluene afforded (S)-2-[3-(2-methoxyphenethylamino)-2-hydroxy-1-propoxy]-3-cyanopyridine (m.p. 97°–99°).

Claims to the invention follow.

I claim:

1. Compounds having the formula

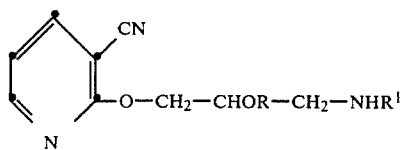

and pharmaceutically acceptable salts thereof
wherein
R is

wherein L is $C_1$–$C_{10}$ alkyl, phenyl or substituted phenyl having one or two substituents independently selected from $C_1$–$C_4$ alkyl, $C_1$–$C_4$ alkoxy or halo $R^1$ is a phenyllinearalkyl group having the formula

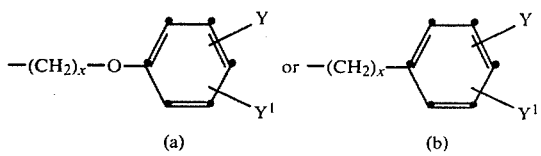

(a)            (b)

wherein
X is 1 to 4 and
Y and $Y^1$ are H, —$OCH_3$, OH or halo.

2. Compounds of claim 1 wherein $R^1$ is

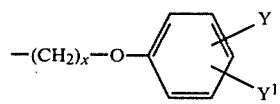

3. Compounds of claim 1 wherein $R^1$ is

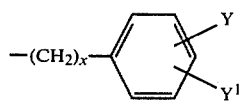

4. Compounds of claim 1 wherein $R^1$ is

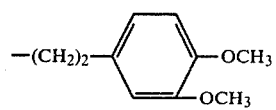

5. Compounds of claim 1 wherein $R^1$ is

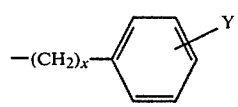

6. Compounds of claim 5 wherein Y is —$OCH_3$.

7. Compounds of claim 6 wherein $R^1$ is

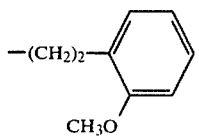

8. The compound of claim 3 having the S-isomer configuration.

9. Pharmaceutical composition for treating hypertension containing an antihypertensive effective amount of a compound of claim 1.

* * * * *